United States Patent [19]
Gilbert

[11] Patent Number: 5,360,013
[45] Date of Patent: Nov. 1, 1994

[54] METHOD AND DEVICE FOR QUALITATIVE DETECTION OF BLOOD IN URINE

[76] Inventor: Edward C. Gilbert, 9706 Logan Dr., Potomac, Md. 20854

[21] Appl. No.: 137,921
[22] Filed: Oct. 19, 1993
[51] Int. Cl.⁵ .............................................. A61B 5/00
[52] U.S. Cl. ...................................... 128/771; 604/318
[58] Field of Search .................. 128/759, 760, 771; 604/168, 189, 318, 404, 900

[56] References Cited

U.S. PATENT DOCUMENTS

| | | | |
|---|---|---|---|
| 3,786,510 | 1/1974 | Hodges | 128/771 |
| 4,417,585 | 11/1983 | Frank | 128/771 |
| 4,808,379 | 2/1989 | Wardlaw et al. | 128/759 |
| 4,832,046 | 5/1989 | Parrish | 128/771 |
| 4,846,005 | 7/1989 | Bacehowski et al. | 128/771 |
| 4,862,899 | 9/1989 | Bucaro | 128/759 |
| 5,119,830 | 6/1992 | Davis | 128/771 |

Primary Examiner—Max Hindenburg
Attorney, Agent, or Firm—Alfred H. Hemingway, Jr.

[57] ABSTRACT

A method and device for qualitatively detecting the presence of blood in urine by comparing the color of the urine to a plurality of colors corresponding to the relative blood content of the urine, which enables a health care provider to roughly identify the stage of hematuria and to decide on an appropriate course of action.

19 Claims, 1 Drawing Sheet

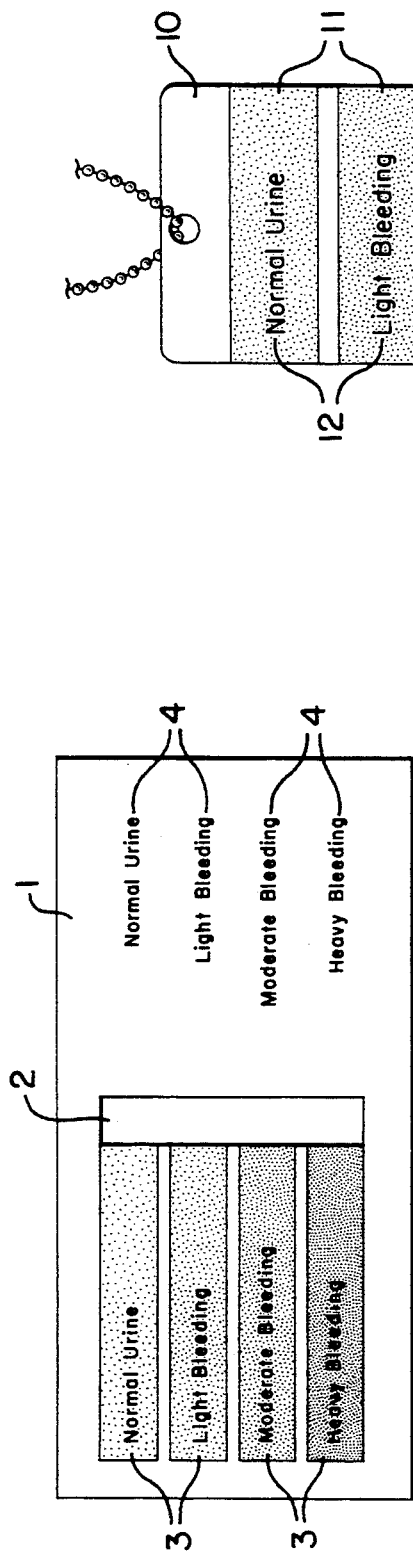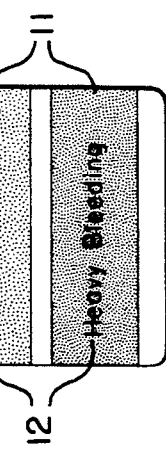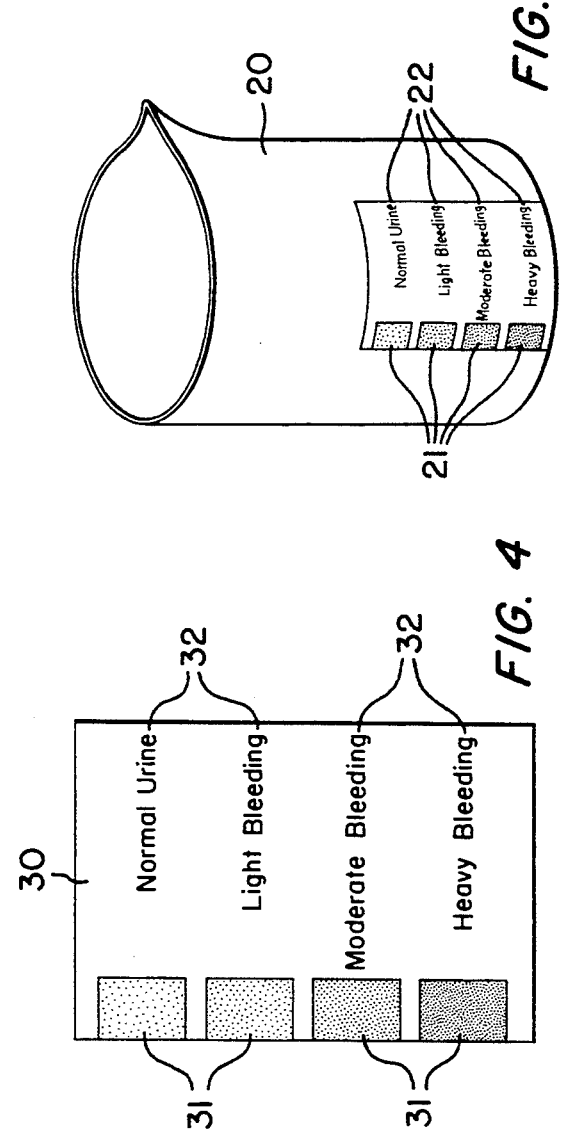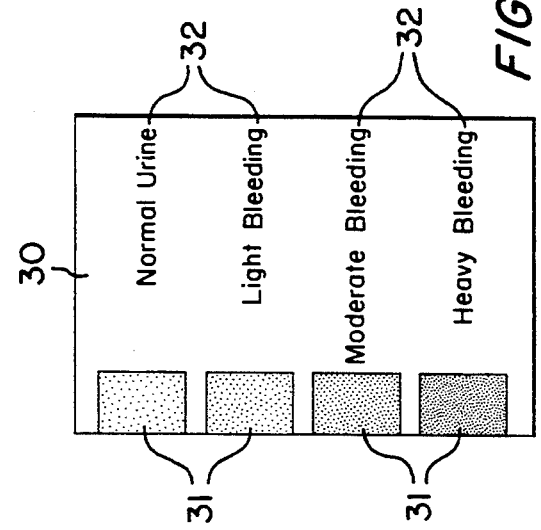

METHOD AND DEVICE FOR QUALITATIVE DETECTION OF BLOOD IN URINE

The present invention is generally directed to a device and method for visually detecting a blood component in body fluids such as urine and more particularly, to a device and method useful in the post-surgery monitoring of recovering patients. The device and method comprise a plurality of colors to be compared to a urine sample of a patient to qualitatively determine the amount of blood in the urine and to aid in the determination of an appropriate course of action.

IN THE DRAWINGS

FIG. 1 shows a device according to the invention designed to be affixed to a tube connecting a urinary catheter and collection device, such as a drainage bag;

FIG. 2 shows a metal or plastic plaque according to the invention, designed to be used as an accessory by health-care providers monitoring the relative blood content of urine;

FIG. 3 shows a transparent container having permanently affixed thereto a color-encoded chart according to the invention; and FIG. 4 represents an embodiment of the invention designed to be affixed to any transparent urine-containing device.

In many surgical procedures involving the genito-urinary tract, such as resection of the prostate or a kidney transplant, a urinary catheter, tube and collection device, such as a drainage bag, are used after surgery to monitor the patient's recovery. During the time of catheterization, the urine flowing in the tube is observed for unusual traces of blood as a measure of the patient's recovery progress. As the healing process continues, the blood content of the urine diminishes or disappears. Several days after the surgical procedure, generally 2-5 days, the catheter is removed from the patient and the urine can be continually monitored to observe urine color and clarity.

The visual inspection of the urine and the assessment of relative blood content based on the appearance of urine output is highly subjective. As the number of health care providers increase, as pressure is brought to bear to forestall the dramatically increasing costs of health care, and with a greater division of responsibility amongst those in health care, there is a greater chance of many different nurses, technicians and pharmacists taking charge of caring for the patient.

Therefore a practical means to quickly and qualitatively assess the presence of a blood component in urine was sought. As a means of reducing the subjective nature of assessing blood content, the present invention utilizes different colors which, after an identification of the closest color match, provides indications such as a relatively high degree of hematuria, suggesting hemoglobin or hematocrit tests and/or intervention by a physician, or of trace amounts of blood, indicating that no action is necessary.

U.S. Pat. Nos. 5,022,411 and 5,133,363 describe rather sophisticated methods for urinalysis in which urine is mixed with labeled antibodies which are colored by a reactant solution to indicate the presence or absence of specific antigens in the urine. While U.S. Pat. No. 4,865,046 is broadly concerned with measuring the blood content in the urine of a catheterized patient, and uses color-coded indicia, the color-coded indicia disclosed are not for assessing blood content.

U.S. Pat. No. 4,473,530 is directed to a urinalysis method in which a powdered stain is added to the urine in order to enhance visual contrast between the constituent elements in a specimen. U.S. Pat. No. 4,417,585 discusses monitoring the urine of a catheterized patient for blood content and describes the use of two color-filtered fiber optic bundles extraneous to the urine flow whose optic ratio is altered by the optical sensing or detection of blood in the urine.

U.S. Pat. No. 4,344,439 discloses the use of a reactive reagent which changes color in the presence of blood in the urine. U.S. Pat. No. 3,786,510 discloses means for measuring the sugar content of a diabetic's urine by using a reagent added to the urine whose color is compared to a color-encoded chart. U.S. Pat. No. 3,266,868 describes color-changing test strips for use in detecting glucose in urine.

It is the principal object of this invention to provide a device which comprises different colors to distinguish among distinct degrees of hematuria.

It is also an object of this invention to provide for an effective means to quickly and objectively determine whether the color of the urine indicates a slight trace of a blood component or a higher level of blood.

It is a further object of this invention to provide a method to determine the existence or severity of hematuria and to allow monitoring health personnel to quickly determine whether tests should be done and/or whether a physician should be notified.

This invention provides a device useful in the qualitative determination of the blood content of urine wherein different colors are compared to the urine and, based upon the closest match, a correct course of action may be determined. A method for objectifying the diagnosis or determination is also provided.

The production of urine in patients is one of the many vital signs monitored in hospitals. Urine production is indicative of renal functions, and also provides useful information regarding liquid balance, perfusion, cardiac output, edema and the like. Clinically, it is important to know the exact volume of urine discharged and the continuum of urine products. It is also important to ascertain the first appearance of a visible blood component in the urine or any change in the appearance of urine which would indicate the presence of a blood component in the kidney or bladder.

The device of the present invention equips the health care provider with a means to compare the color of the urine being discharged from a catheter and tube, and/or collected in a container or other urinalysis unit, to reference colors. The color codes contain colors representing possible colors of urine samples, such as from yellow to deep red. One end of the continuum, e.g., the yellow, indicates unremarkable urine discharge, while the other end of the continuum, e.g., deep red, represents significantly bloody urine. Having a continuum of representative colors with which to compare the urine sample allows for a more objective, qualitative detection of blood content. The device can also be encoded with other colors to denote the urine sample.

The device allows for greater standardization in the qualitative determination of blood in the urine. Rather than having the individual perceptions of color by health care providers control the assessment of urine color, and thereby a determination of the relative blood content of the urine, this device provides a rough guide to describe the condition and, for example, to suggest to the user whether blood tests should be run and/or whether the patient's condition should be brought to the attention of a physician.

In addition to providing descriptors, i.e., means to categorize the color of the urine, the device may also provide directions for courses of action depending upon the color. For example, a yellow urine sample would be deemed unremarkable output and a direction could indicate that no further action except for continued monitoring should be taken. However, a deep red color could indicate an emergency situation in which a doctor should be summoned immediately. An intermediate color might suggest that blood tests, such as hemoglobin and/or hematocrit, would be in order. The direction of any color shift in the urine would also indicate to monitoring health care providers whether the patient is progressing in recovery or has a worsening condition.

This invention will be better understood by reference to the following examples, which are included here for purposes of exemplification and are not to be construed as limitations.

One embodiment of the device of the present invention is pictured in FIG. 1. This embodiment is intended to be attached to tubing connecting a catheter implanted in a patient with a collection device, such as a drainage bag. It is attached by means of adhesive located on the back of the device. The middle area comprises a transparent window so as to enable viewing the urine passing from the catheter to the collection device. The color-encoded chart 1 is positioned with the window 2 longitudinally along the tubing so as to allow one to directly compare the color of urine passing in the tubing and viewed through the window with the nearby plurality of colors 3. On the color-encoded chart, as well as opposite the color-encoded chart, are descriptors 4 corresponding to the color of the urine. For example, FIG. 1 shows the placement of the color coding, the transparent window and the descriptors for the health care provider as to what the colors signify. The descriptors may be designed to be identical to the colors of the coding chart in order to simplify the device.

A further embodiment involves a device which is not physically attached to any collection means. In many instances, health care providers carry stethoscopes or other portable diagnostic instruments. A device according to the invention, such as in the form of a color-coded metal or plastic plaque 10 as shown in FIG. 2, may also be carried by a health care provider responsible for monitoring the urine of patients for blood content and compared to the patient's urine sample, whether in a catheter tube, a drainage bag or as collected in any transparent container. As shown in this embodiment, the plaque 10 comprises a plurality of appropriate colors 11 and descriptors 12.

The invention could also be utilized by providing a transparent reusable device for containing urine, such as a test tube, beaker or the like, having colors according to the invention permanently affixed to the container, as shown in FIG. 3. This embodiment comprises a transparent beaker 20 having a plurality of colors 21 permanently attached to it, such as by a decal or being printed thereon, along with descriptors 22 and/or directions. Alternatively, a color-encoded, adhesive-backed chart as shown in FIG. 4 could be affixed to the outside of a transparent urine-containing device. The FIG. 4 embodiment shows a thin, flexible chart 30 bearing a plurality of appropriate colors 31 and descriptors 32. The back of chart 30 comprises a permanent or releasable adhesive by which the chart may be permanently or temporarily affixed to a transparent, urine-containing device.

It is also possible to devise different forms of a color-encoded chart or device to achieve the same or a similar purpose. Therefore, the embodiments set forth in the examples should not be construed as limitations. It is not intended that the present invention be limited to only the described embodiments. Modification of these embodiments will be recognized by those skilled in the art. Rather, the invention should be circumscribed by the scope of the appended claims.

I claim:

1. A device for the qualitative determination of the amount of blood in visually bloody urine comprising a plurality of colors corresponding to the relative blood content of the urine.

2. The device of claim 1, further comprising adhesive means for attaching said device to a transparent urine-containing device.

3. A device for the qualitative determination of the amount of blood in visually bloody urine, comprising means for assessing the color of the urine with respect to its relative blood content and means for aiding in the determination of an appropriate course of action.

4. The device of claim 3, further comprising adhesive means for attaching said device to a transparent urine-containing device.

5. A device for the qualitative determination of the amount of blood in visually bloody urine, comprising:
   (a) means for assessing the relative blood content of the urine;
   (b) means for aiding in the determination of an appropriate course of action depending upon said relative blood content; and
   (c) means for attaching said device to a transparent urine-containing device.

6. A device according to claim 5, wherein said means for assessing the relative blood content of urine comprises a plurality of colors.

7. A device according to claim 6, wherein said means for aiding in the determination of an appropriate course of action comprise descriptors written on said device.

8. A device according to claim 6, wherein said means for attaching said device to a transparent urine-containing device comprise an adhesive.

9. A device according to claim 5, wherein said means for aiding in the determination of an appropriate course of action comprise descriptors written on said device.

10. A device according to claim 5, wherein said means for attaching said device to a transparent urine-containing device comprise an adhesive.

11. The combination of a transparent urine-containing device and means for qualitatively determining the amount of blood in visually bloody urine, said means comprising a plurality of colors corresponding to the relative blood content of the urine.

12. A combination according to claim 11, wherein said means further comprise an adhesive for affixing said means to said device.

13. A combination according to claim 12, wherein said adhesive is a releasable adhesive.

14. A method for the visual, qualitative determination of a blood component present in visually bloody urine, comprising visually comparing a urine sample to a plurality of colors corresponding to the relative blood content of the urine.

15. The method of claim 14, wherein the plurality of colors is affixed to a device selected from the group consisting of a flexible chart, a plaque and a transparent, urine-containing device.

16. A method according to claim 15 comprising the additional step of following directions accompanying said colors.

17. A method according to claim 15 comprising the additional step of utilizing descriptors accompanying said colors.

18. A method according to claim 14 comprising the additional step of following directions accompanying said colors.

19. A method according to claim 14 comprising the additional step of utilizing descriptors accompanying said colors.

* * * * *